United States Patent [19]

Makiej, Jr.

[11] Patent Number: 4,936,461

[45] Date of Patent: Jun. 26, 1990

[54] MULTIDOSE CAPSULES

[76] Inventor: Walter J. Makiej, Jr., 70 Mount Hope, Lowell, Mass.

[21] Appl. No.: 363,539

[22] Filed: Jun. 8, 1989

Related U.S. Application Data

[60] Continuation-in-part of Ser. No. 189,963, Dec. 23, 1988, abandoned, Continuation-in-part of Ser. No. 082,034, Aug. 5, 1987, Pat. No. 4,793,493, which is a division of Ser. No. 908,823, Sep. 8, 1986, abandoned.

[51] Int. Cl.⁵ .............................................. B65D 85/42
[52] U.S. Cl. .................... 206/528; 206/602; 424/467
[58] Field of Search ............... 206/219, 222, 528, 530, 206/532, 538, 539, 602; 220/4 D, 20, 22; 424/467, 468

[56] References Cited

U.S. PATENT DOCUMENTS

| | | | |
|---|---|---|---|
| 1,510,260 | 9/1924 | Cyrenius | 206/528 |
| 1,861,047 | 5/1932 | Colton | 206/528 |
| 1,867,494 | 7/1932 | Buchner | 206/77.1 |
| 2,594,093 | 4/1952 | Thompson | 206/528 |
| 2,640,623 | 6/1953 | Ryder | 206/602 |
| 2,726,004 | 12/1965 | McLeod | 220/23.2 |
| 2,753,868 | 7/1956 | Seemar | 206/222 |
| 3,072,528 | 1/1963 | Kludas et al. | 206/528 |
| 4,793,493 | 12/1988 | Makiej, Jr. | 206/528 |

Primary Examiner—David T. Fidei
Attorney, Agent, or Firm—Jason M. Honeyman

[57] ABSTRACT

The present invention is a multidose capsule. The capsule consists of a longitudinally extending tube and caps for each end thereof. An intermediate section of the longitudinally extending tube is severable so that the capsule may be broken into two separately administrable components.

12 Claims, 1 Drawing Sheet

MULTIDOSE CAPSULES

CROSS-REFERENCE TO RELATED APPLICATIONS

This application is a continuation-in-part of Ser. No. 289,963 filed on Dec. 23, 1988, now abandoned, Ser. No. 289,963 is a continuation-in-part application of Ser. No. 082,034 filed on Aug. 5, 1987, which issued on Dec. 27, 1988 as U.S. Pat. No. 4,793,493; Ser. No. 082,034 is a divisional application of Ser. No. 908,823 filed on Sept. 8, 1986, which application is abandoned. The teachings of Ser. No. 082,034, Ser. No. 289,963 and Ser. No. 908,823 are hereby incorporated by reference.

FIELD OF ART

The present invention relates to medicinal capsules and, more particularly, relates to medicinal capsules for use in the titration of individualized drugs.

BACKGROUND OF THE ART

It is well known in the art that the dose required of certain drugs to achieve and maintain therapeutic and safe levels varies significantly from patient to patient. Because overdosing of such drugs can cause a myriad of severe side effects including nausea, vomiting, convulsions, ventricular arrhythmias, seizures and cardiorespiratory arrest, the maximum effective dose to be administered is ordinarily determined on an individualized basis. Theophylline, a drug used primarily as a bronchodilator, is typical of such individualized medications.

The present method for individualizing theophylline is by titration. During titration, the patient is given an initial dose of theophylline which, dependent upon serum theophylline measurement, is adjusted either upwardly or downwardly. Subsequent doses of theophylline are then accordingly increased or decreased until the maximum therapeutic dose is achieved. Unfortunately, each adjustment of the dose level during the titration cycle requires the patient to purchase a separate and distinct potency capsule since conventional capsules can only deliver a single predetermined theophylline dose. The cost for titrating theophylline in conventional capsule form can therefore become prohibitive, especially considering the fact that capsules of theophylline are ordinarily sold only in large quantities having a uniform potency.

An additional problem with the conventional capsules used to titrate theophylline is that oral administration of the drug by sprinkling fails to deliver the entire dose carried by the capsule. Regardless of the capsule orientation, removal of either end of the conventional capsule results in a significant quantity of the drug medium escaping over the edges of the capsule housing. Consequently, it is difficult to ascertain the exact dosage which is ultimately administered to the patient. Moreover, a patient may be tempted to administer a second dose of theophylline to compensate for the inadequate delivery of the first dose. Sprinkling theophylline or other individualized drugs from conventional capsules therefore poses a serious health risk to the patient, especially considering the severe side effects associated with overdose of such medications.

SUMMARY OF THE INVENTION

The present invention is a capsule for carrying multiple or graduating doses of medicinal particles, beads or liquids. In one important embodiment of the invention, the capsule includes a hard gelatin tube having a first end and a second end and a frangible dividing section, supported by the tube, which divides the tube into first and second chambers. The frangible dividing section comprises a first wall and a second wall spaced therefrom. A portion of the periphery of the hard gelatin tube located between the first and second walls is scored or notched to facilitate rupturing of the dividing section therealong under an applied stress. Snapping of the tube in an axial direction causes the frangible dividing section to fracture, thereby separating the multidose capsule into first and second capsule remnants as defined by the first and second chambers, respectively. The patient can administer the drug by either removing the caps from the capsule remnants and sprinkling or by leaving the caps on the remnants and ingesting the remnants whole.

Accordingly, it is a primary object of the present invention to provide a capsule for carrying multiple or varying doses of medication.

It is another object of the present invention to provide a capsule which can be administered orally by either swallowing the capsule or sprinkling the medicinal medium contained within the capsule.

It is another object of the present invention to provide a capsule which is easily administrable to either geriatric, pediatric, tube fed patients or other individuals who have difficulty swallowing capsules whole.

It is another object of the present invention to provide a capsule which facilitates titration to the appropriate level without requiring the use of additional capsules having either increased or decreased dosage levels.

It is a still further object of the present invention to provide an inexpensive capsule that can be easily separated by the patient into varying predetermined doses.

BRIEF DESCRIPTION OF THE DRAWINGS

These and other details of the invention will be described in connection with the accompanying drawing in which.

DESCRIPTION OF THE PREFERRED EMBODIMENT

Figure 1:
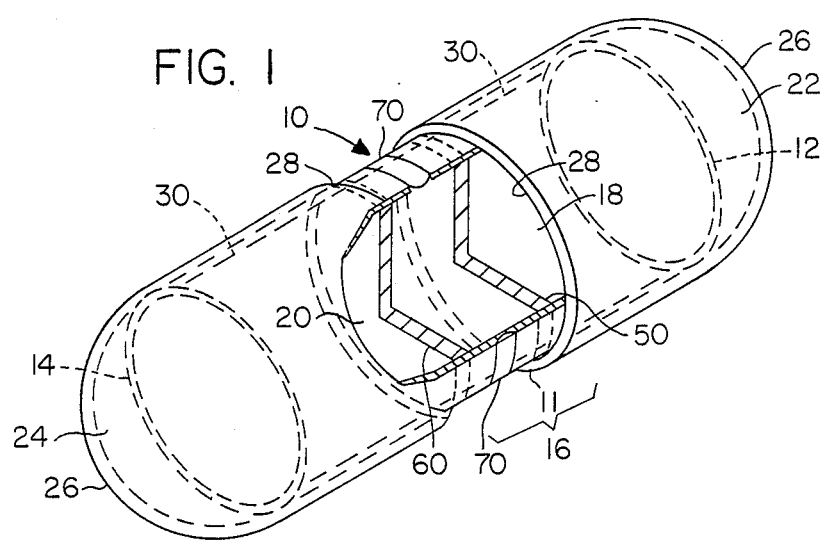
FIG. 1 is a perspective view, partly in section, showing the capsule according to the preferred embodiment of the invention.

The present invention is a capsule for carrying multiple or graduating doses of a desired drug in either liquid, solid or particle form. In the preferred embodiment shown in FIG. 1, the capsule 10 includes a tube 11 having a first end 12 and a second end 14 and a dividing section 16 that separates the tube 11 into a first chamber 18 and a second chamber 20 which, preferably, are volumetric equivalents. The first chamber 18 is filled with the desired drug in either powder, particle or liquid form by any conventional means such as a Type 8 Standard Hard Capsule Filling Machine, distributed by Warner Lambert Company, or other capsule filling apparatus as is known to those skilled in the art. Subsequent to filling the first chamber 18 with the desired dose, removably supportable cap 22 is slidably mounted upon and along the first end 12 of tube 11. After the first chamber 18 has been sealed by the removably supportable cap 22, the second chamber 20 is accordingly filled with the appropriate dose level of the desired medication. The second removably supportable cap 24 is then slidably mounted upon and along the second end 14 of tube 11 to seal the second chamber 20. The resulting capsule 10 is therefore divided into two separate chambers, preferably containing equal volumetric amounts of the desired medication.

Dividing section 16 includes first wall 50 and second wall 60 spaced therefrom. Preferably, a portion 70 of the periphery of the tube extending between the first wall 50 and second wall 60 is scored or notched with respect thereto to render the tube periphery frangible therealong. Although the tube periphery relative to the first wall 50 and second wall 60 is preferably notched or scored, other means of increasing the frangibility of the tube at this locus may, alternatively, be utilized. In that the tube interior between first wall 50 and second wall 60 is empty, and therefore consists of dead space, the dividing section 16 is easily frangible upon application of an appropriate stress.

Tube 11, first wall 50, second wall 60 and removably supportable caps 22, 24 are each preferably fabricated from a hard gelatin material such as type A gelatin, type B gelatin or mixtures thereof. The gelatin may be either dyed or dye free dependent upon the ultimate application. Alternatively, the capsule components can be formed from other conventional materials as is known to those skilled in the art. The first and second walls 50, 60 are preferably formed integral with the tube 11 in the manufacturing process. Alternatively, first and second walls 50, 60 may constitute separate elements having dimensions congruous to, but slightly larger than, the cross section of the tube whereby these walls are retainable in spaced relationship in annular channels in the interior periphery of the tube 11. Removably supportable caps 22, 24 are sealed at one end 26 and are opened at the other end 28. The sealed end 26 being rounded or constructed on a section of a sphere as in conventional capsules. Open end 28 is preferably flexible at least to the extent sufficient to facilitate mounting and sliding of the caps along the ends and extension 30 of the tube when sealing the chambers. In the preferred embodiment, the diameter of each of the removably supportable caps 22, 24 is slightly greater than the diameter of the associated tube end 12, 14 to enable mounting of the cap on the tube end thereunder. The resilient force of the open end 28 against the tube ends 12, 14 and tube extension 30 is sufficient to retain the caps 22, 24 on the tube 11 thereunder.

Multidose capsule 10 may be administered orally to the patient by either swallowing the capsule whole or by, instead, removing caps 22, 24 and sprinkling the drug beads contained therein into the mouth of the patient, onto a soft food carrier, through a nasal gastric tube or by other means known to those skilled in the art. The sprinkling capability of the multidose capsule 10 is especially beneficial for geriatric and pediatric patients who have great difficulty swallowing capsules as well as for nasal gastric fed patients who cannot swallow such capsules.

Frangible dividing section 16 is easily fracturable in half to allow the capsule 10 to be split into separate remnant units defined by the first and second chambers. Application of an appropriate stress along the dividing section midplane, typically by snapping the tube along the scored or notched periphery thereof between the first and second walls 50, 60, will result in separating the capsule into two separate single-dose capsule remnants. The single-dose capsule remnants are sealed at one end by the removably supportable caps 64, 66 and at the other end by the respective first or second wall 50, 60. The single-dose capsules may be either swallowed in whole, or the medicinal contents may alternatively be received by sprinkling.

Figure 2:
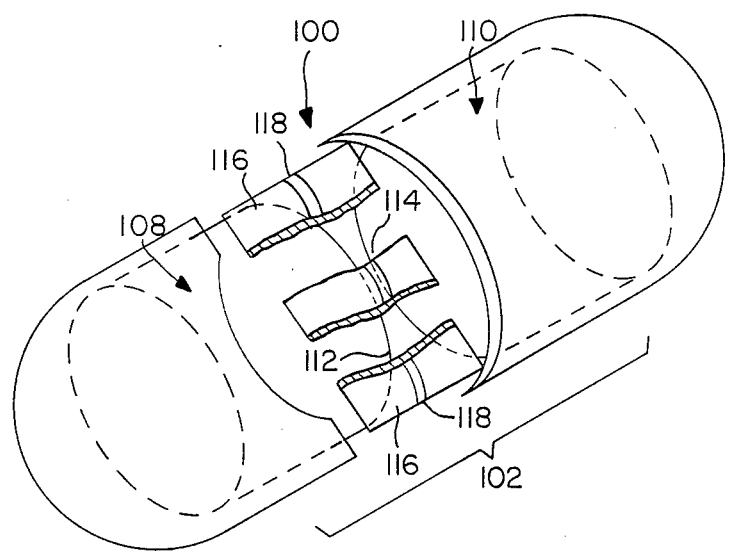
FIG. 2 is a perspective view, partly in section, showing the capsule according to an alternative embodiment of the invention

An alternative embodiment of the multidose capsule is shown in FIG. 2. Multidose capsule 100 includes hollow tube 102 formed from aligned capsule halves 108, 110. Rounded ends 112, 114 are supported together by hard gelatin band 116 disposed annularly therealong. Rounded ends 112, 114 are held by the hard gelatin band 116 in contact with one another or, preferably, spaced apart to facilitate application of the fracturing stress to the dividing section. Hard gelatin band 116 is scored or notched 118 along the periphery thereof relative to the rounded ends 112, 114 to render the tube 102 frangible therealong.

In the preferred embodiment, the first and second chambers of the multidose capsule are volumetric equivalents. Hence, the dose of medicinal particles, beads or liquid deliverable from each chamber is, equivalent. By administration of the drug contained in only one of the chambers, a single predetermined dose of medication may be delivered. Conversely, sprinkling or swallowing the contents of both chambers will result in a double dose of medication being administered. A triple dose of medication may be obtained by administering both chambers of one multidose capsule and one chamber of a second multidose capsule of equivalent dose capability. Additional multiple doses of medication are thereby provided by administration of further multidose capsule chambers. Varying the volume of the first and second chambers so that they are not equivalent further optimizes the spectrum of doses which can be delivered.

In the preferred embodiment, the deliverable dose of each chamber is 50 milligrams (mg) of medication. Of course, in alternative embodiments, varying chamber sizes, including those capable of delivering 25 mg, 60 mg, 75 mg, etc., of beads, particles or liquid may be utilized. Moreover, the dose provided by the first and second chambers need not be equivalent. Hence the first chamber may contain 75 mg of drug while the second chamber may contain only 25 mg of medication. Such a multidose capsule is therefore capable of delivering graduating doses of either 25 mg, 75 mg or 100 mg of the desired medication.

The multidose capsule, by providing graduating doses of medication in a single capsule, is particularly attractive for use in the oral administration of theophylline and other individualized drugs which require titration by the patient before the appropriate level of medication can be determined. In a typical titration cycle for theophylline, a multidose capsule having a first chamber containing 25 mg of drug and a second chamber containing 75 mg of medication is utilized for delivering the initial dose of 100 mg. The multidose capsule is administered by having the patient swallow the capsule whole or by sprinkling the drug contained in each chamber onto a food carrier which is then ingested by the patient. If the drug is not tolerated at this dose level, the next scheduled theophylline administration will consist of a decreased dose, preferably by 25%. This is easily accomplished with the multidose capsule by either breaking the capsule along the dividing wall and having the patient swallow the chamber remnant containing 75 mg of theophylline or by simply removing the removably supportable cap enclosing the 75 mg chamber and orally administering the theophylline by known sprinkling techniques. Conversely, if the initial dose of theophylline is too low, the subsequent dose administered to the patient will be increased. The increased dose, ordinarily 25%, may again be administered by either breaking off a 25 mg chamber from a multidose capsule and having the patient swallow the 25 mg remnant along with an unbroken 100 mg multidose capsule or by sprinkling the contents of the multidose capsule onto a food carrier along with the contents of a 25 mg chamber from an additional capsule. Further adjustments to the theophylline dose level until the maximum acceptable dose is reached are administered accordingly.

It is understood that the preceding description is given merely by way of illustration and not in limitation of the invention and that various modifications may be made thereto without departing from the spirit of the invention as claimed.

What is claimed is:

1. An ingestable hard gelatin capsule for holding medication to be ingested which comprises:
    a longitudinally extending tube having a first end and a second end;
    at least one dividing section intermediate said first and second ends which separates said longitudinally extending tube into a first and second chamber, said at least one dividing section including a first wall and a second wall, said first and second wall extending through said longitudinally extending tube, said longitudinally extending tube having means for severing a portion of the periphery of said longitudinally extending tube relative to said first and second walls; and
    first and second removably supportable caps, each of said first and second removably supportable caps having a first open end and a second sealed end, said open end of said first removably supportable cap being slidable along and mountable upon said first end of said longitudinally extending tube and said open end of said second removably supportable cap being slidable along and mountable upon said second end of said longitudinally extending tube to an extent sufficient to support each of said first and second removably supportable caps on said longitudinally extending tube thereunder.

2. The invention as recited in claim 1 wherein said means for severing includes said portion of said periphery of said longitudinally extending tube relative to said first and second walls being scored.

3. The invention as recited in claim 1 wherein said means for severing includes said portion of said periphery of said longitudinally extending tube relative to said first and second walls being notched.

4. The invention as recited in claim 1 wherein said first wall is spaced from said second wall.

5. The invention as recited in claim 1 wherein said first and second walls extend in cross-sectional planes through said longitudinally extending tube.

6. The invention as recited in claim 1 wherein said first and second walls are rounded.

7. An ingestable hard gelatin capsule for holding medication to be ingested which comprises:
    first and second longitudinally extending hollow tubes, each of said first and second longitudinally extending hollow tubes having an open end and a closed rounded end;
    means, extending from said first longitudinally extending hollow tube to said second longitudinally extending hollow tube, for supporting said closed rounded ends relative to one another, said supporting means including means for severing said supporting means along a cross-sectional plane thereof; and
    first and second removably supportable caps, each of said first and second removably supportable caps having a first open end and a second sealed end, said open end of said first removably supportable cap being slidable along and mountable upon said open end of said first longitudinally extending hollow tube and said open end of said second removably supportable cap being slidable along and mountable upon said open end of said second longitudinally extending hollow tube to an extent sufficient to support each of said first and second removably supportable caps on said first and second longitudinally extending hollow tubes thereunder.

8. The capsule as recited in claim 7 wherein said means for supporting includes a hard gelatin band annularly disposed along said closed rounded ends of said first and second longitudinally extending hollow tubes and said means for severing includes notches in said hard gelatin band.

9. The capsule as recited in claim 7 wherein said means for supporting includes a hard gelatin band annularly disposed along said closed rounded ends of said first and second longitudinally extending hollow tubes and said means for severing includes a scored periphery of said hard gelatin band.

10. The capsule as recited in claim 7 wherein said means for supporting includes means for supporting said rounded ends in spaced alignment.

11. The capsule as recited in claim 7 wherein said means for supporting includes means for supporting said rounded ends in longitudinal alignment.

12. An ingestable hard gelatin capsule for holding medication to be ingested which comprises:
    first and second longitudinally extending hollow tubes, each of said first and second longitudinally extending hollow tubes having an open end and a closed rounded end;
    a hard gelatin band extending longitudinally from said closed rounded end of said first longitudinally extending hollow tube to said closed rounded end of said second longitudinally extending hollow tube, said closed rounded ends being supported in spaced longitudingal alignment with one another by said hard gelatin band, said hard gelatin band including means for severing said hard gelatin band along a cross-sectional plane thereof; and
    first and second removably supportable caps, each of said first and second removably supportable caps having a first open end and a second sealed end, said open end of said first removably supportable cap being slidable along and mountable upon said open end of said first longitudinally extending hollow tube and said open end of said second removably supportable cap being slidable along and mountable upon said open end of said second longitudinally extending hollow tube to an extent sufficient to support each of said first and second removably supportable caps on said longitudinally extending hollow tubes thereunder.

* * * * *